United States Patent
Jensen

(10) Patent No.: US 9,714,909 B2
(45) Date of Patent: Jul. 25, 2017

(54) METHOD OF DETERMINING CATALYTIC FINES IN AN OIL

(71) Applicant: Nanonord A/S, Alborg (DK)

(72) Inventor: Ole Norgaard Jensen, Alborg (DK)

(73) Assignee: NANONORD A/S, Alborg (DK)

(*) Notice: Subject to any disclaimer, the term of this patent is extended or adjusted under 35 U.S.C. 154(b) by 531 days.

(21) Appl. No.: 14/364,102

(22) PCT Filed: Dec. 7, 2012

(86) PCT No.: PCT/DK2012/050456
§ 371 (c)(1),
(2) Date: Jun. 10, 2014

(87) PCT Pub. No.: WO2013/087077
PCT Pub. Date: Jun. 20, 2013

(65) Prior Publication Data
US 2014/0333304 A1    Nov. 13, 2014

(30) Foreign Application Priority Data
Dec. 12, 2011 (DK) .................. 2011 00964

(51) Int. Cl.
*G01V 3/00* (2006.01)
*G01N 24/08* (2006.01)
*G01N 33/28* (2006.01)

(52) U.S. Cl.
CPC ......... *G01N 24/082* (2013.01); *G01N 24/085* (2013.01); *G01N 33/2829* (2013.01)

(58) Field of Classification Search
USPC ........................................ 324/309
See application file for complete search history.

(56) References Cited

U.S. PATENT DOCUMENTS 3,858,111 A * 12/1974 Simpson, Jr. .......... G01R 33/46
                                                     324/310
5,023,551 A    6/1991   Kleinberg
(Continued)

FOREIGN PATENT DOCUMENTS

CA    1085614      9/1980
GB    2467527 A    8/2010
(Continued)

OTHER PUBLICATIONS

Bruker DRX 600 MHz Spectrometer, 1999, http://cbc.arizona.edu/rss/nmr/manuals/Drx600Intro.pdf.*
(Continued)

*Primary Examiner* — Rodney Fuller
(74) *Attorney, Agent, or Firm* — Pearne & Gordon LLP

(57) ABSTRACT

The invention concerns a method of performing a quantitative and/or qualitative determination of catalytic fines in fuel oil and a system suitable for determining catalytic fines in an oil using the method.

The method comprises determining aluminum using NMR and quantitatively and/or qualitatively determining the catalytic fines based on the aluminum determination.

The system comprises a NMR spectrometer, a digital memory storing a calibration map comprising calibrating data for calibrating NMR spectra obtained by the NMR spectrometer and a computer programmed to analyze the NMR spectra obtained by the NMR spectrometer using calibration map and performing at least one quantitative and/or qualitative catalytic fines determination.

44 Claims, 9 Drawing Sheets

(56) References Cited

U.S. PATENT DOCUMENTS

| | | | | |
|---|---|---|---|---|
| 5,124,026 | A * | 6/1992 | Taylor | C10G 67/049 208/162 |
| 5,124,027 | A * | 6/1992 | Beaton | C10G 67/049 208/162 |
| 5,391,304 | A * | 2/1995 | Lantos | B01D 3/06 210/774 |
| 6,268,913 | B1 | 7/2001 | Rising | |
| 6,310,480 | B1 * | 10/2001 | Cohen | G01R 33/31 324/318 |
| 7,750,634 | B1 * | 7/2010 | Christensen | G01N 24/08 324/307 |
| 2003/0006768 | A1 * | 1/2003 | Kleinberg | G01N 24/081 324/303 |
| 2004/0090231 | A1 * | 5/2004 | Augustine | G01N 24/08 324/309 |
| 2004/0119471 | A1 * | 6/2004 | Blanz | E21B 49/00 324/303 |
| 2008/0224696 | A1 * | 9/2008 | Edwards | G01R 33/441 324/303 |
| 2009/0118556 | A1 * | 5/2009 | Euzen | B01J 21/12 585/251 |
| 2009/0120836 | A1 * | 5/2009 | Weber | C10G 31/08 208/13 |
| 2009/0179636 | A1 | 7/2009 | Chen | |
| 2009/0256562 | A1 * | 10/2009 | Gao | G01N 24/08 324/308 |
| 2010/0085047 | A1 | 4/2010 | Nikolin | |
| 2011/0137003 | A1 | 6/2011 | Collins | |

FOREIGN PATENT DOCUMENTS

| | | | |
|---|---|---|---|
| GB | 2474343 | A | 4/2011 |
| JP | 63-088435 | A | 4/1988 |
| JP | 07-333178 | A | 12/1995 |
| JP | 2005-030815 | A | 2/2005 |
| JP | 2009-041985 | A | 2/2009 |
| JP | 2011-080766 | A | 4/2011 |
| JP | 2011-095170 | A | 5/2011 |
| KR | 2004-0027054 | A | 4/2004 |
| WO | 2009/015185 | A2 | 1/2009 |
| WO | 2010021768 | A1 | 2/2010 |

OTHER PUBLICATIONS

Translation of First Office Action issued in corresponding Chinese Patent Application No. 201280069391.1 dated Nov. 3, 2015.
H. Y. Carr et al. "Effects of Diffusion on Free Precession in Nuclear Magnetic Resonance Experiments" Physical Review, vol. 94, No. 3 dated May 1, 1954.
George R. Coates et al. "NMR Logging Principles & Applications" Halliburton Energy Services, 1999.
E.L. Hahn. et al. "Spin Echoes", Physical Review, vol. 80, No. 4 dated Nov. 15, 1950.
Danish Search Report issued in Application No. PA 2011 00964 dated Jun. 12, 2012.
International Search Report issued in Application No. PCT/DK2012/050456 dated Mar. 5, 2013.
Danish Search Report issued in Application No. PA 2012 70535 dated Apr. 18, 2013.
International Search Report issued in Application No. PCT/DK2012/050452 dated Mar. 5, 2013.
"Standard Test Method for Determination of Nickel, Vanadium, Iron, and Sodium in Crude Oils and Residual Fuels by Flame Absorption Spectrometry" Designation :D5863-00a, Published by ASTM International, May 2011.
Extended European Search Report for 12 85 6813 dated Jul. 31, 2015.

* cited by examiner

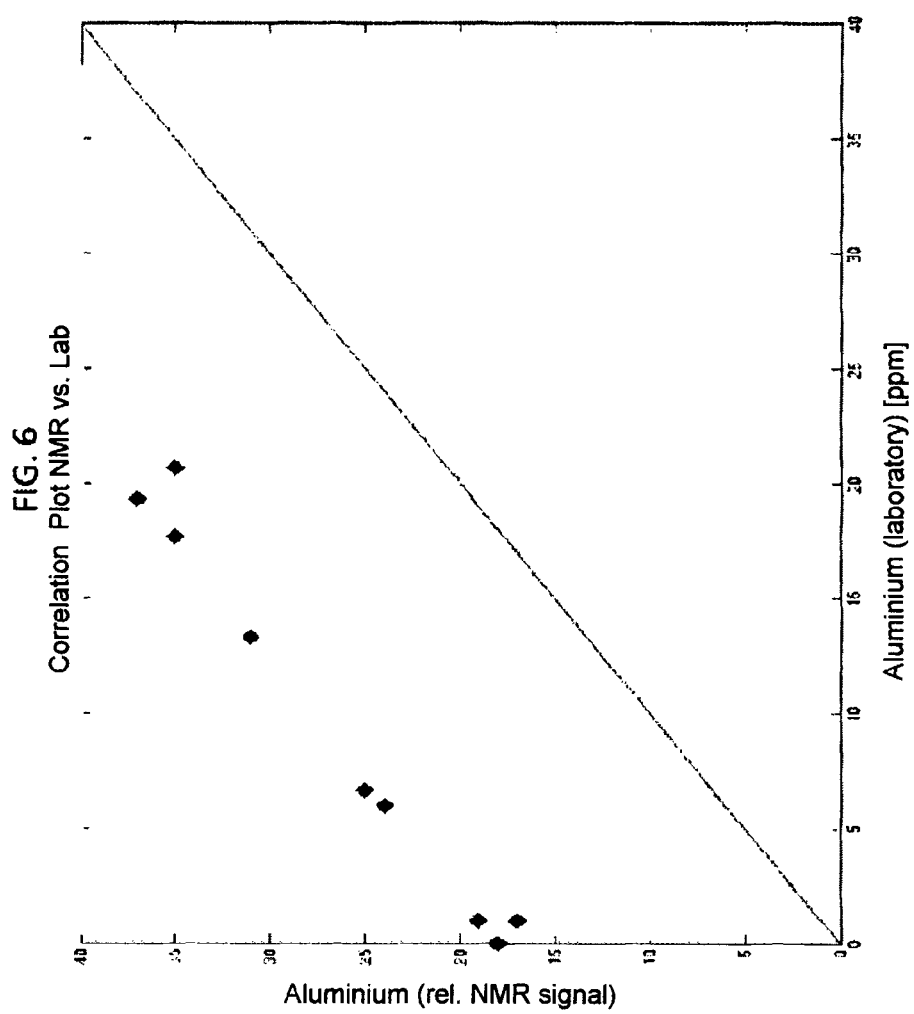

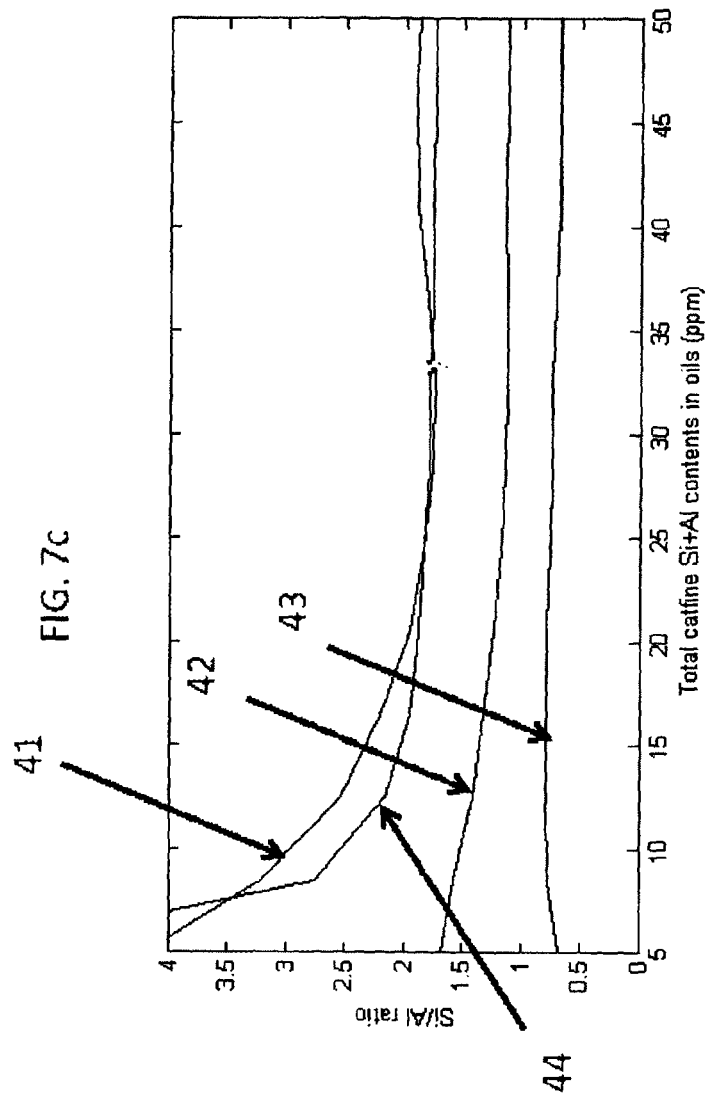

METHOD OF DETERMINING CATALYTIC FINES IN AN OIL

TECHNICAL FIELD

The invention relates to a method and a system for quantitative and/or qualitative determination of catalytic fines in fuel oil, in particular heavy fuel oil.

BACKGROUND ART

Fuel oil is a fraction of oil obtained from oil refining process, either as a distillate or a residue and is often used as fuel for power stations, marine engines and similar. The aim of a catalytic cracker in refinery processing is to increase the quantity of lighter constituents or gasoline from the crude processed. While the intention is to retain the catalyst particles or fines, often simply called "cat fines", in the catalytic cracker due to the high cost of the replacement of the material, this is not entirely possible to do so.

In particular the heavier part of the fuel oil, which is also referred to as "HFO", often comprises considerable amounts of catalytic fines. The catalytic fines are hard, abrasive crystalline particles of alumina, silica, and/or alumina silica that can be carried over from the fluidic catalytic cracking process of residual fuel stocks. Particle size can range from sub-micron to greater than sixty microns in size. These particles become more common the higher the viscosity of the oil. HFO is often used as motor fuel e.g. in the marine industry, for example as fuel in vessels in which situation the HFO is called bunker fuel, which is the heaviest part of the oil. Also certain lighter oil types can comprise catalytic fines e.g. Marine Diesel Oil (MDO), which is a middle distillate fuel oil which can contain certain amounts, such as 5-10% by volume of residual fuel oil from transportation contamination and/or heavy fuel oil blending. The catalytic fines often accumulate in the fuel tanks which may give rise to very high concentrations of catalytic fines.

The hard abrasive catalytic fines can cause increased and at times severe wear in the engine as well as in fuel pumps, delivery valves, fuel injectors, piston rings, piston rods and other parts in contact with the HFO.

It is not only the amount of the catalytic fines that is important; the nominal size of the particles may also be relevant. The size of the particles can vary from very small (less than a micron) to larger than 60 microns. The main part of the catalytic fines is expected to be relatively spherical, however, it has also been observed that some parts of the catalytic fines can be elongated and with a small cross sectional area in one direction such catalytic fines can pass through even the finest filters and cause damage to the engine.

ISO 8217:2010 recommendation (http://www.dnv.com/industry/maritime/servicessolutions/fueltesting/fuelqualitytesting/iso8217fuelstandard.asp) specifies that the content of catalytic fines in the fuel oil delivered on board may not exceed a maximum of 60 ppm (w/w). Marine engine manufactures typically recommend that HFO oils that are consumed shall have less than 15 ppm of catalytic fines.

Therefore several cleaning or extraction systems for reducing the amount of catalytic fines in the fuel oil have been provided e.g. on board the vessels.

Centrifuges in combination with a settling tank are generally accepted within the marine industry as the fuel cleaning system of choice. Filters are mainly considered as a safety to pick up larger particles so that these particles do not reach the engine, and do not as such "clean" the fuel.

Other extracting/cleaning systems include the separators described in US 2009/0120836 as well as the separators marketed by Alfa Laval under the name S-separator and P-separator for marine use.

Even though large efforts are made to remove catalytic fines it is practically impossible to remove all catalytic fines.

If properly operated, an extracting device has the capability to remove catalytic fines that are larger than 10 microns. However, the majority of catalytic fines smaller than five microns will not be removed due to small size and their relative light weight.

Furthermore it is very difficult to determine the amount of catalytic fines in fuel oil. Today the only way to obtain a reasonable determination of the amount of catalytic fines in a fuel, is to send a test sample to a dedicated laboratory. The test performed is based on general chemistry analytic methods and is generally a very time consuming and expensive test and only a few laboratories offer such tests.

The object of the invention is to provide a new and reliable method for determining catalytic fines in fuel oil. In particular the object of the invention is to provide a method for determining catalytic fines in fuel oil where the determination can be performed on the location in a relative simple way.

DISCLOSURE OF INVENTION

This object has been solved by the present invention as defined in the claims. The method of the invention and embodiments thereof as well as the system for determining catalytic fines of the invention and embodiments thereof have shown to have a large number of advantages which will be clear from the following description.

As explained above, before providing the present invention was conceived, the determination of catalytic fines in fuel oil has been very difficult and cumbersome. Due to the present invention determination of catalytic fines in fuel oil can now be performed on location e.g. on board a vessel and much faster than using the prior art methods. In practice the method of the invention has shown to be operable in nearly real-time.

In an embodiment of the invention the method is applied to provide a level of the catalytic fines in a fuel oil.

In an embodiment of the invention the method is applied to determine the total content or concentration of catalytic fines in a fuel oil.

It has been found that by use of the method of the invention, even very small catalytic fines particles can be included in the determination.

Even though the phenomenon of Nuclear Magnetic Resonance (NMR) is well known and is also well known to apply in determination of isotopes by spectroscopy e.g. for use in determining organic compounds using proton $^1$H NMR or $^{13}$C NMR, it has heretofore never been suggested or even considered possible to apply NMR in determination of catalytic fines in HFO. The present invention therefore opens up for a completely new and reliable method of determining catalytic fines and thereby provide a large improvement compared to prior art method. Due to the present invention it is now possible to determine the level, type and/or amount of catalytic fines on the location.

The inventor of the present invention has found that the result obtained by providing a quantitative and/or qualitative NMR determination of aluminum in the fuel oil in fact can provide a corresponding quantitative and/or qualitative determination of catalytic fines in the fuel oil.

In an embodiment the method of the invention is for use in a laboratory, which provides an alternative and cost effective method compared to prior art laborious methods.

The method of performing a quantitative and/or qualitative determination of catalytic fines in fuel oil comprises determining aluminum using NMR and quantitative and/or qualitative determination of the catalytic fines based on the aluminum determination.

As it will be explained in more detail below, the signal obtained in the aluminum determination can be correlated directly to catalytic fines or it can be correlated to the aluminum and from the aluminum to the catalytic fines in a quantitative and/or qualitative correlation.

Nuclear magnetic resonance—abbreviated NMR—is a phenomenon which occurs when the nuclei of certain atoms are immersed in a static magnetic field and exposed to a second oscillating magnetic field. NMR measurement is performed by NMR spectroscopy and comprises using the NMR phenomenon to study materials e.g. for analyzing organic chemical structures The method of the invention preferably comprises determining aluminum in the form of aluminum isotope $^{27}Al$ by performing at least one NMR measurement (spectroscopy) on a part of the oil. The performing of the NMR measurement results in obtaining at least one NMR spectrum from the NMR measurement. The term "NMR spectrum" is herein used to designate the signal obtained from an NMR measurement. The NMR spectrum may be in the form of part(s) of or all of a physical drawn spectrum, it may be in the form of part(s) of or all of a spectrum in digital form, it may be in the form of peak determinations or results derived there from or in any other form in which the resulting signals or parts thereof obtained from an NMR measurement can be provided. Such NMR spectra are well known in the art.

In an embodiment of the method the one or more NMR spectra obtained are used to perform at least one quantitative and/or qualitative aluminum determination. The at least one quantitative and/or qualitative aluminum determination can thereafter be used to determine the catalytic fines quantitatively and/or qualitatively.

In an embodiment of the method the one or more NMR spectra obtained are used directly to determine the catalytic fines quantitatively and/or qualitatively.

The method of determining the catalytic fines from the one or more NMR spectra obtained will be described in more details below.

Spectrometers are well known in the art and the skilled person will be able to select a suitable spectrometer for use in the present invention based on the teaching provided herein. Examples of spectrometer are e.g. described in U.S. Pat. No. 6,310,480 and in U.S. Pat. No. 5,023,551.

A spectrometer comprises a unit for providing a permanent field e.g. a permanent magnet assembly as well as a transmitter and a receiver for transmitting and/or receiving RF frequency pulses/signals The RF receiver and RF transmitter are connected to an antenna or an array of RF antennae, which may be in the form of transceivers capable of both transmitting and receiving. The spectrometer further comprises at least one computing element, in the following referred to as a computer.

General background of NMR formation evaluation can be found, for example in U.S. Pat. No. 5,023,551.

Although 'NMR measurement' in the following often will be used in singular to describe the invention, it should be observed that the singular term 'NMR measurement' also includes a plurality of NMR measurements unless other is specified.

In an embodiment of the invention the NMR measurement is performed on the oil part in flowing condition. The NMR measurement may for example be performed on the oil part during transportation from a first container to a second container or to a point of use, such as to a second storage container or to use in an engine.

The second storage container can for example be a refinery or a service tank. In an embodiment the NMR measurement is performed on the oil part in flowing condition in a pipe section pumping the oil from a first container and back to the same first container.

In an embodiment the NMR measurement is performed on the oil part in flowing condition in a pipe section pumping the oil from a first container to a second container of a refinery.

In an embodiment the NMR measurement is performed on the oil par during loading e.g. fuelling of the oil.

When performing the NMR measurement on the oil part in flowing condition it should be ensured that the velocity of the flowing oil is adjusted or kept such that the oil part is within the spectrometer for a sufficient time to perform the NMR measurement.

In an embodiment of the invention the NMR measurement is performed in-line or semi-in-line, comprising performing the NMR measurement onboard a motor driven unit, such as a vessel.

The term "in-line" should herein be interpreted to mean that the NMR measurement is performed directly on the oil part without removing the oil part from the remaining oil. The NMR measurement may e.g. be performed on the oil part in flowing condition as described above or it may be performed directly on the oil part in a container e.g. near the bottom of a container comprising the fuel oil. As the catalytic fines have a tendency to accumulate in the bottom part of containers or in corners, crooks or recesses, it may in an embodiment be desired to perform the NMR measurement in-line on such part of oil containing equipment.

In an embodiment the NMR measurement is performed in-line directly on the oil part in flowing condition e.g. in a pipe or directly on the oil part in a container comprising the oil onboard the motor driven unit.

The term "semi-in-line" should herein be interpreted to mean that NMR measurement is performed on the oil part temporally withdrawn from the remaining oil, performing at least one NMR measurement and optionally returning the oil sample to the remaining part of the oil, wherein for a plurality of consecutive NMR measurements on consecutively withdrawn oil parts at least some of the oil parts, such as a plurality, such as about 90% or more, the oil parts are returned to the remaining part of the oil.

In an embodiment the NMR measurement is performed semi-in-line by temporally withdrawing the oil part as a sample of the oil, performing the NMR measurement on the withdrawn sample and optionally returning the oil sample to the remaining part of the oil, where the oil part preferably is withdrawn from a container comprising the oil onboard the motor driven unit.

According to the invention it has been found to be very beneficial that the NMR measurement can be performed directly onboard a vessel. The determination of catalytic fines can be performed as a continuous process which thereby provides a very economically attractive system, which simultaneously provides a high safety against catalytic fines destroying parts of the engines or other equipment in contact with the fuel oil.

In an embodiment of the invention the NMR measurement comprises withdrawing the oil part as a sample of the oil and performing the NMR measurement on the withdrawn sample. In this embodiment the oil part may e.g. be sent to a laboratory for having the NMR measurement performed.

In an embodiment of the invention onboard determination of catalytic fines is combined with ad hoc controlling laboratory catalytic fine determinations which laboratory catalytic fine determinations may be performed using traditional prior art methods or which laboratory catalytic fine determinations may be performed using NMR according to the invention. For cost effective determinations the latter method will generally be preferred.

In an embodiment of the invention the method comprises repetitive determinations of catalytic fines, e.g. for observing changes of the type, level and/or level of catalytic fines in the oil.

In an embodiment the method comprises determining catalytic fines in the oil, subjecting the oil to a catalytic fine extraction treatment, and repeating the determination of catalytic fines in the oil.

The process of extracting catalytic fines is also referred to a purifying the fuel oil. The extraction treatment can be any kind of extracting or cleaning treatment suitable for extracting catalytic fines from fuel oil, such as heavy fuel oil or diesel.

The extraction treatment may for example be performed by separators such as traditional centrifuges in combination with a settling tank or by using separators, such as the separators described in US 2009/0120836 or the separators marketed by Alfa Laval under the name S-separator and P-separator for marine use. Extraction treatment may preferably be provided to reduce the amount of catalytic fines to a level sufficient to fulfill the recommendation of ISO 8217, i.e. such that the amount of catalytic fines does not exceed a maximum of 60 ppm. When the parameter determined as parts per million is used herein the parts per million are determined in W/W unless other is specified. In a preferred embodiment the extraction treatment is provided to reduce the amount of catalytic fines to about 15 ppm or less.

By repeating the catalytic fine determination the effect of the extraction can be determined and as described further below the catalytic fine determinations may even be applied to optimize the performance of the extraction process. This method will be described in further detail below.

In an embodiment NMR measurement comprises simultaneously subjecting the oil part to a magnetic field B and a plurality of pulses of radio frequency energy E (in form of RF pulses) and receiving electromagnetic signals from the aluminum isotopes.

In an embodiment the method comprises determining the amount of aluminum isotopes in the sample part and correlating the amount of aluminum to an amount of catalytic fines.

RF pulses mean herein pulses of radio frequency energy.

In order to obtain NMR spectra of a high resolution (i.e. as low noise as possible) it is generally desired that the NMR measurements are performed using a relatively high magnetic field B.

In an embodiment the magnetic field B is at least about 1 Tesla, such as at least about 1.2 Tesla, such as at least about 1.4 Tesla, such as at least about 1.6 Tesla.

The magnetic field B may be generated by any suitable means. The magnetic field B is in a preferred embodiment between about 1 and about 3 Tesla, such as between about 1.5 and 2.5 Tesla.

In an embodiment the magnetic field is generated by a permanent magnet, such as a neodymium magnet. Since permanent magnets are generally not costly, this solution provides a low cost solution which for many applications may provide a sufficient low noise result.

In an embodiment the magnetic field is generated by an electromagnet, such as a solenoid magnet or other electromagnets which are usually applied in motors, generators, transformers, loudspeakers or similar equipment. Electromagnets of high strength e.g. electromagnets that can be applied for generating a field of about 1.5 Tesla or more are often relatively expensive compared with permanent magnets. However, the magnetic field generated using electromagnets can be both relatively strong and relatively homogeneous simultaneously, which is very beneficial in the present invention.

Furthermore, the electromagnet may be adjusted by adjusting the current in the coil of the electromagnet to a desired level.

In a preferred embodiment the magnetic field is generated by an electromagnet in form of a superconducting magnet comprising a coil of superconducting wire. Such superconducting magnets are well known in the art and can be made to produce relatively high magnetic fields. Furthermore such superconducting magnets can provide a very homogeneous field and simultaneously they are relatively cheaper to operate because almost no energy dissipates as heat in windings of the coils.

Examples of superconducting magnets suitable in the present invention are disclosed in GB 2474343 or in GB 2467527.

In an embodiment of the invention the magnetic field in the measuring zone, i.e. the part where the oil part is located when the NMR measurement is performed, is preferably relatively spatially homogeneous and relatively temporally constant. However, in general it is difficult to provide that the magnetic field in the measuring zone is entirely homogenous and further for most magnetic fields, the field strength might drift or vary over time due to aging of the magnet, movement of metal objects near the magnet, and temperature fluctuations.

Drift and variations over time can be dealt with by controlling temperature and/or by applying a field lock such as it is generally known in the art.

Spatial inhomogeneities of the magnetic field can be corrected for by a simple calibration or alternatively or simultaneously such spatial inhomogeneities can be adjusted for by shim coils such as it is also known in the art. Such shim coils may e.g. be adjusted by the computer to maximize the homogeneity of the magnetic field.

In an embodiment of the invention the method comprises performing a plurality of NMR measurements at a selected magnetic field, preferably the magnetic field is kept substantially stationary during the plurality of NMR measurements.

In an embodiment the method of the invention comprises regulating the temperature e.g. by maintaining the temperature at a selected value.

In an embodiment the method of the invention comprises determining the temperature.

The term 'substantially' is herein used to include ordinary variations and tolerances which are normally accepted within the art in question.

In an embodiment the method comprises performing a plurality of NMR measurements on the same oil. In practice the NMR measurement of the oil will be performed a plurality of times in order to reduce the noise. In an embodiment the NMR measurement is performed continuously in repeated measuring cycles. In an embodiment the method comprises performing a plurality of NMR measurements on the same oil part. The NMR measurements are normally performed very fast e.g. several NMR measurement circles per second, such as 20 NMR measurements or more, such as 50 NMR measurements or more. Therefore even when performing the NMR measurement on the oil part in flowing condition, several NMR measurements may be performed on virtually the same oil part.

In an embodiment the NMR measurement comprises simultaneously subjecting the oil part to a magnetic field B and an exciting RF pulse with frequencies selected to excite a nuclei spin of at least a part of the aluminum isotopes, preferably the exciting RF pulse has a band width (span over a frequency range) which is sufficient to excite at least one nuclei spin (spin transition) of substantially all aluminum isotopes in the oil part.

In theory one single exciting RF pulse can be sufficient to obtain a useful signal. In an embodiment of the invention it is desired to use a sequence of RF pulses with frequencies having a selected band width in order to excite a desired number of nuclei spin of the aluminum isotopes in the oil part.

A general background description of NMR measurement can be found in "NMR Logging Principles and Applications" by George R. Coates et al, Halliburton Energy Services, 1999. See in particular chapter 4. Although this document does not specifically describe the NMR determination of aluminum isotope, the principle applied is similar.

Since the aluminum isotope has an electric quardrupole moment, it has several nuclei spins which may be excited at equal or at different frequencies in dependence on the environment of the aluminum isotope, i.e. the compound it is part of. It is said that the nuclei spins of the aluminum isotope are shifted due to quadrupolar couplings when the nuclei spins of the aluminum isotope are excited at different frequencies.

Quadrupole Splitting reflects the interaction between the nuclear energy levels and surrounding electric field gradient (EFG). Nuclei in states with non-spherical charge distributions, such as aluminum isotope with angular quantum number (I) of 5/2, produce an asymmetrical electric field which splits the nuclear energy levels. This produces a nuclear quadrupole moment. The quadrupole moment interacts anisotropicall (orientation dependent) with the EFG, resulting in optional splitting up of signals from an aluminum isotope, dependent on its position in a compound and in particular dependent on the symmetry of the compound. The splitting up of signals from an aluminum isotope is called the quadrupole broadening.

In an embodiment the oil part is subjected to an exciting RF pulse with frequencies selected to excite at least one nuclei spin of substantially all aluminum isotopes in the oil part. Preferably the oil part is subjected to an exciting RF pulse with frequencies selected to excite the aluminum isotopes in their central band, such that at least a central (seen in relation to the exciting frequency) nuclei spin of the aluminum isotopes in the oil part is excited. Nuclei spins of the aluminum isotopes that are not in the central band are said to be in side bands.

In an embodiment the oil part is subjected to an exciting RF pulse with frequencies selected to excite a plurality nuclei spins of substantially all aluminum isotopes in the oil part. Preferably the oil part is subjected to an exciting RF pulse with frequencies selected to excite the aluminum isotopes at least in their central band and at least to excite one or more nuclei spins of the aluminum isotope in their side bands.

In an embodiment the oil part is subjected to an exciting RF pulse with frequencies selected to excite substantially all nuclei spins of substantially all aluminum isotopes in the oil part.

A sufficient frequency range of radio pulses (band width) can be found by performing a calibration test on oil with known catalytic fines that is desired to be determined. The aluminum isotope of the aluminum silicate catalytic fines normally will be excited at least in their central bands within a relatively small frequency range of radio pulses.

Chemical shift is defined as the relative difference in resonant frequency compared to a reference signal. The shift is believed to be caused by spin-spin coupling between protons of compounds.

Chemical shifts of the exciting due to the bonding of the Al isotopes in compounds are generally so small that such chemical shifts can be ignored.

Inhomogeneities of the magnetic field should normally also be accounted for when selecting the band width.

In an embodiment the radio frequency pulses are in form of adiabatic RF pulses, i.e. RF pulses that are amplitude and frequency modulated pulses.

As mentioned above aluminum isotope is a spin 5/2 nucleus and is therefore quadrupolar. As a result, the signal width increases with asymmetry of the environment with small or somewhat broad lines in symmetrical environments but very broad lines in asymmetric ones. This effect is generally known in the art.

Also the presence of other components, such as salt and water in the oil can result in antenna detuning and provisions shall be made to automatically keep track of this tuning and adjust match, if necessary.

In an embodiment of the invention the frequency range of the exciting RF pulse spans over at least about 10000 ppm, preferably at least about 50000 ppm, such as from about 2000 ppm to about 50000 ppm.

The span of frequencies as well as a frequency shift is often measured in ppm—i.e. with respect to a reference compound.

Based on the teaching provided herein, the skilled person will be able to select a frequency range of the exciting RF pulse which is sufficient to obtain a reliable determination of catalytic fines in a fuel oil.

In an embodiment of the invention the frequency range of the exciting RF pulse comprises a band width of at least about 1 MHZ.

By a few trial and error tests the desired frequency range for at specific type of determination can be found.

The actual frequencies that are exiting the spin of the aluminum isotope nucleus depend largely on the magnetic field B. As explained above, the magnetic field may vary due to drift and due to temperature variations and it is generally preferred that the exciting RF pulses are adjusted by a field lock function in order to ensure that the NMR measurements are performed using exciting RF pulses which are directed towards desired nucleus spin of the alumina.

For example in an embodiment where the magnetic field is from about 1 T to about 2 T, the exciting RF pulse preferably comprises at least some of the frequencies in the range from about 10 MHz to about 22 MHz, such as at least a frequency band width of at least about 1 MHZ. In an embodiment where the magnetic field is from about 1 T to about 2 T, the exciting RF pulse comprises at least some of the frequencies in the range from about 13 MHz to about 19 MHz.

In an embodiment the method of the invention comprises determining at least one relaxation rate of an exited aluminum isotope.

The term relaxation describes processes by which nuclear magnetization excited to a non-equilibrium state return to the equilibrium distribution. In other words, relaxation describes how fast spins "forget" the direction in which they are oriented. Methods of measuring relaxation times T1 and T2 are well known in the art.

In an embodiment the method comprises determining at least one spin-lattice-T1 relaxation value of an exited aluminum isotope.

It is believed that T1 relaxation involves redistributing the populations of nuclear spin states in order to reach the thermal equilibrium distribution.

T1 relaxation values may be dependent on the NMR frequency applied for exciting the aluminum isotope. This should preferably be accounted for when analyzing and calibrating the T1 relaxation values obtained.

In an embodiment the method comprises determining at least one spin-spin-T2 relaxation value of an exited aluminum isotope.

The T2 relaxation is also called the transverse relaxation.

Generally T2 relaxation is a complex phenomenon and involves decoherence of transverse nuclear spin magnetization. T2 relaxation values are substantially not dependent on the magnetic field applied during excition of the aluminum isotope, and for most determinations such possible variations can be ignored.

In an embodiment the method comprises subjecting the oil part to pulsed trains of RF pulses, preferably with repetition rates of at about 100 ms or less, such as from about 10 to about 50 ms, such as from about 15 to about 20 ms.

The trains of RF pulses are often applied to determine the T1 and/or T2 values.

In an embodiment, the method comprises subjecting the oil part to trains of square RF pulses, preferably with repetition rates of about 100 ms or less, such as about 10 ms or less, such as about 5 ms or less.

A short square pulse of a given "carrier" frequency "contains" a range of frequencies centered about the carrier frequency, with the range of excitation (bandwidth/frequency spectrum) being inversely proportional to the pulse duration.

In the present invention it is in an embodiment desired that the carrier frequency is from about 13 MHz to about 19 MHz and the duration is from about 5 µs to about 20 µs when the magnetic field is from about 1 to about 2 T. The frequencies can be regulated accordingly if another magnetic field is applied.

A Fourier transform of an approximately square wave contains contributions from all the frequencies in the neighborhood of the principal frequency. The restricted range of the NMR frequencies made it relatively easy to use short (millisecond to microsecond) radio frequency pulses to excite the entire NMR spectrum.

In an embodiment the NMR measurement comprises simultaneously subjecting the oil part to a magnetic field B and a plurality of RF pulses wherein the RF pulses comprise
  i. an exciting RF pulse, and
  ii. at least one refocusing RF pulse.

The exciting RF pulse and the refocusing pulse or pulses may for example be in the form of a train of RF pulses, e.g. pulsed pulses. The exciting RF pulse is preferably as described above and may in an embodiment be pulsed.

Useful duration and amplitude of the exciting RF pulses are well known in the art and optimization can be done by a simple trial and error.

In an embodiment the exciting RF pulse is in the form of a 90° pulse.

A 90° pulse is an RF pulse designed to rotate the net magnetization vector 90° from its initial direction in the rotating frame of reference. If the spins are initially aligned with the static magnetic field, this pulse produces transverse magnetization and free induction decay (FID).

In an embodiment the refocusing RF pulse(s) is in the form of a 180° pulse, preferably the method comprises subjecting the oil part to a plurality of refocusing RF pulses, such as one or more trains of refocusing RF pulses.

A 90° pulse is an RF pulse designed to rotate the net magnetization vector 180° in the rotating frame of reference. Ideally, the amplitude of a 180° pulse multiplied by its duration is twice the amplitude of a 90° pulse multiplied by its duration. Each 180° pulse in the sequence (called a CPMG sequence after Carr-Purcell-Meiboom-Gill) creates an echo.

A standard technique for measuring the spin-spin relaxation time T2 utilizing CPMG sequence is as follows. As is well known after a wait time that precedes each pulse sequence, a 90-degree exciting pulse is emitted by an RF antenna, which causes the spins to start processing in the transverse plane. After a delay, an initial 180-degree pulse is emitted by the RF antenna. The initial 180-degree pulse causes the spins, which are dephasing in the transverse plane, to reverse direction and to refocus and subsequently cause an initial spin echo to appear. A second 180-degree refocusing pulse can be emitted by the RF antenna, which subsequently causes a second spin echo to appear. Thereafter, the RF antenna emits a series of 180-degree pulses separated by a short time delay. This series of 180-degree pulses repeatedly reverse the spins, causing a series of "spin echoes" to appear. The train of spin echoes is measured and processed to determine the spin-spin relaxation time T2

In an embodiment the refocusing RF pulse(s) is/are applied with an echo-delay time after the exciting RF pulse. The echo-delay time (also called wait time TW) is preferably of about 50 µs or less.

This method is generally called the "spin echo" method and was first described by Erwin Hahn in 1950. Further information can be found in Hahn, E. L. (1950). "Spin echoes". Physical Review 80: 580-594, which is hereby incorporated by reference.

A typical echo-delay time is from about 10 µs to about 50 ms, preferably from about 50 µs to about 200 µs. The echo-delay time (also called wait time TW) is the time between the last CPMG 180° pulse and the first CPMG pulse of the next experiment at the same frequency. This time is the time during which magnetic polarization or T1 recovery takes place. It is also known as polarization time.

This basic spin echo method provides very good result for obtaining T1 relaxation values by varying TW and T2 relaxation values can also be obtained by using plurality of refocusing pulses.

In an embodiment the at least one refocusing pulse comprises a plurality of refocusing pulses or trains of refocusing pulses applied with refocusing delay (TE) intervals between two consecutive refocusing pulses.

The refocusing delay is also called the Echo Spacing and indicates the time identical to the time between adjacent echoes. In a CPMG sequence, the TE is also the time between 180° pulses.

This method is an improvement of the spin echo method by Hahn. This method was provided by Carr and Purcell and provides an improved determination of the T2 relaxation values.

Further information about the Carr and Purcell method can be found in Carr, H. Y.; Purcell, E. M. (1954). "Effects of Diffusion on Free Precession in Nuclear Magnetic Resonance Experiments". Physical Review 94: 630-638, which is hereby incorporated by reference.

A typical refocusing delay interval is from about 50 μs to about 0.1 ms, preferably about 75 μs.

In an embodiment the NMR measurement comprises a repeating exciting-refocusing sequence each exciting-refocusing sequence comprises
 i. an exciting RF pulse, and
 ii. at least one refocusing RF pulse.

The exciting-refocusing sequence is preferably repeated a plurality of times such as at least 100 times, such as at last 200 or preferably much more.

In order to reduce noise it is generally desired to repeat the exciting-refocusing sequence 5.000 times or more. In an embodiment of the invention the exciting-refocusing sequence is repeated with 5 to 500 exciting-refocusing sequences per second, such as with 50 to 400 exciting-refocusing sequences per second, such as with 150 to 250 exciting-refocusing sequences per second.

In an embodiment the exciting-refocusing sequence is repeated from about 5 minutes to about 24 hours, such as typically from about 1 hour to about 10 hours.

The higher magnetic field strength in the measuring zone the better the signal to noise ratio will be and in general the fewer repetitive NMR measurements are needed. In general the noise will be reduced with the square number of repeated NMR measurements For determination of an indication of catalytic fines in an oil, the number of repetitions of the exciting-refocusing sequence can be held relatively low, however, such 'fast' determination will normally not provide exact results, but will most often only be used as a first indication or an indication of a substantial change of catalytic fines amount in the tested oil.

The number of repeating NMR measurement for a given determination versus the time requires can be optimized by the skilled person.

In an embodiment the method comprises obtaining at least one NMR spectrum obtained in relation to a reference Al-composition, wherein the reference Al-composition preferably is Zeolite Y.

In an embodiment the method comprises determining quantitatively and/or qualitatively at least one compound comprising an aluminum isotope. According to the invention it is anticipated that by comparing the result obtained by the NMR measurement of a given oil with corresponding NMR measurements of oil with known types of catalytic fines, it can be deduced which type of catalytic fines are present in the given oil in question.

In this connection the NMR measurements of oil with known types of catalytic fines are used as a calibration map which can be stored in a computer for calibrating the NMR measurements of a given sample.

In an embodiment of the invention the method comprises determination of catalytic fines comprising a quantitative and/or qualitative determination of at least one aluminum containing compound and/or at least one aluminum containing complex, such as aluminum contained in minerals or zeolites, such as minerals contain aluminum and silicon oxides, such as hydrated aluminosilicates, optionally comprising K, Na, Ca or V or trapped positive ions: H+, Na+, K+, Ca2+, Cu2+ or Mg2+.

In an embodiment the NMR measurements of oil with known types of catalytic fines are used to teach an artificial intelligent computer or a neural network to recognize the pattern of the specific type of catalytic fines detected for.

In an embodiment the method comprises performing a quantitative and/or qualitative aluminum determination. The quantitative and/or qualitative aluminum determination is preferably performed by providing a calibration map of known aluminum containing compound(s) and optionally of amounts thereof in oil.

The term 'calibrating map' is herein used to designate a collection of NMR spectra data obtained in oil with known amount/type of aluminum and/or catalytic fines. The calibration map may be in form of raw data, in form of drawings, in form of graphs, in form of formulas or any combinations thereof.

Generally it is well known in the art to calibrate the NMR measurements of an $^{27}AL$ NMR measurement to obtain a determination of the amount of aluminum isotope in the tested oil part.

The calibration map may be in the form of a plurality of distinctive determinations, NMR spectra for samples with known amount or type of aluminum.

In an embodiment the calibration map is in the form of a pre-processed data set, where the NMR spectra obtained for an oil under analysis can be processed by the computer to provide a clear level of the aluminum in the oil.

The determination of alumina can be correlated to find a quantitative and/or qualitative amount/type of catalytic fines. This can be provided by an additional data map. For example it has surprisingly been found that the molar amount of aluminum in a simple way can be correlated to the molar amount of silicon (Si) in the oil, and based on this the amount of catalytic fines can be determined.

In an embodiment, the oil used for generating the calibrating map is of a similar type as the oil to be tested. In an embodiment the calibration map also comprises a plurality of values for determination made on oil with water.

In an embodiment the method comprises performing a quantitative and/or qualitative catalytic fine determination directly from the NMR spectra obtained. The quantitative and/or qualitative catalytic fine determination is preferably performed by providing a calibration map of known catalytic fine compound(s) and optionally of amounts thereof in oil.

In an embodiment the method comprises preparing calibration data, the calibration data is preferably stored on a digital memory, the method comprises feeding the NMR spectrum(s) or data obtained from the NMR spectra to a computer in digital communication with the digital memory and providing the computer to compare and analyze the data to perform at least one quantitative and/or qualitative aluminum determination.

The calibration map may be built up during use, for example additional data obtained by measurement on the oil is fed to the computer and used in the calibration of the data and thereby the determination of catalytic fines.

The computer may for example be programmed to compute the data obtained using artificial intelligence or the calibration map may be applied to teach a neural network. In particular for qualitative determination it is in an embodiment desired that the computer is programmed to use artificial intelligence to recognize the pattern of a specific type of catalytic fines.

In an embodiment the method comprises performing at least one NMR measurement on a plurality of oil parts, preferably the method comprises performing a plurality of NMR measurements and optionally other measurements, such as hydrogen measurement for qualitative/quantity measurements on a plurality of oil parts.

In order to improve the determination in the oil, other compounds can additionally and preferably simultaneously be determined in the oil.

In an embodiment the method further comprises performing a sodium determination of measurement on the oil part using NMR, preferably by determining $^{23}$Na isotope by performing at least one NMR measurement on the oil part, obtaining at least one NMR spectrum from the NMR measurement(s) and performing at least one quantitative and/or qualitative sodium determination. The NMR measurement preferably comprises obtaining at least one spin-lattice-T1 value and at least one spin-spin-T2 value of an exited sodium isotope.

Sodium determination using NMR can be performed in a similar manner as the method described above but by using other frequencies and optionally the strength of the magnetic field may also be adjusted. The skilled person will know how to perform such determinations. In an embodiment the determination of sodium is performed using the same hardware (magnet, pulse emitter, receiver and similar) as used in the aluminum determination. Thereby the equipment and the set up can be economical feasible.

In an embodiment the method further comprises performing a vanadium determination of measurement on the oil part using NMR, preferably by determining $^{51}$V isotope by performing at least one NMR measurement on the oil part, obtaining at least one NMR spectrum from the NMR measurement(s) and performing at least one quantitative and/or qualitative sodium determination. The NMR measurement preferably comprises obtaining at least one spin-lattice-T1 value and at least one spin-spin-T2 value of an exited vanadium isotope.

Vanadium determination using NMR can be performed in a similar manner as the method described above but by using other frequencies and optionally the strength of the magnetic field may also be adjusted. The skilled person will know how to perform such determinations. In an embodiment the determination of vanadium is performed using the same hardware (magnet, pulse emitter, receiver and similar) as used in the aluminum determination. Thereby the equipment and the set up can be economical feasible.

In an embodiment the method comprises obtaining at least one NMR spectrum of $^{27}$Al isotope and obtaining at least one NMR spectrum using an NMR equipment comprising an NMR spectrometer, comprising at least a magnet, a pulse emitter and a receiver, wherein the method further comprises obtaining at least one NMR spectrum of at least one other isotope using at least a part of the NMR equipment. The at least one other isotope is preferably selected from $^{23}$Na isotope, $^{51}$V isotope and $^{63}$Cu isotope.

Although catalytic fines can be found in many oils, the method of the invention is in particular provided for analyzing fuel oil such as heavy fuel oil (HFO), suitable for use as bunker fuel.

In an embodiment the method comprises performing a quantitative determination of catalytic fines in the oil. The determination will preferably provide a result in ppm.

In an embodiment the method comprises
i. performing a quantitative and/or qualitative determination of catalytic fines in the oil before extraction;
ii. extracting catalytic fines from the oil; and
iii. performing a quantitative and/or qualitative determination of catalytic fines in the oil after extraction.

In an embodiment the method comprises
i. performing a quantitative and/or qualitative determination of catalytic fines in the oil;
ii. subjecting the oil to an extraction of catalytic fines in a separator operating with a number of operating parameters comprising pressure, flow velocity and temperature;
iii. performing a quantitative and/or qualitative determination of catalytic fines in the oil;
iv. comparing the determinations performed before the extraction with the determination performed after the extraction to determine the performance of the separator; and
v. adjusting one or more of the operating parameters of the separator based on the determination of the separator performance.

The method using a separator may be as described in the forgoing. In the above embodiment the performance of the separator can be optimized. Until the present invention such an optimization of the performance of the separator has in practice not been possible or at least such an optimization has been both extremely time consuming and rather expensive.

In the present invention the optimization can be applied as a routine for such separators, and the optimization can be performed on a continuous basis.

In an embodiment steps i-v are repeated in two or more cycles and the determinations of the separator performance for several previous cycles are used in the step of adjusting one or more of the operating parameters of the separator to optimize the performance of the separator.

In an embodiment of the method of the invention of performing a quantitative and/or qualitative determination of catalytic fines in an oil, the method comprises performing at least one quantitative and/or qualitative aluminum determination and performing a quantitative and/or qualitative determination of catalytic fines in the oil based on the determination of aluminum and a calibration map of previous determinations of aluminum.

The method will be further exemplified below.

The invention also relates to a system suitable for determining catalytic fines in an oil. The system of the invention is suitable for carrying out the method for determining catalytic fines in an oil described above.

The system of the invention comprises a NMR spectrometer, a digital memory storing a calibration map comprising calibrating data for calibrating NMR spectra obtained by the NMR spectrometer and a computer programmed to analyze the NMR spectra obtained by the NMR spectrometer using calibration map and performing at least one quantitative and/or qualitative catalytic fines determination.

The spectrometer may be as described above and should preferably be configured to performing a NMR measurement of an oil part of a suitable volume. The calibration map may be as described above.

The calibration map may be continuously updated with new data.

The system may comprise one, two or more computers, one two or more spectrometers and/or one, two or more calibration maps.

The system may preferably be in data communication with the internet e.g. for communication with other similar systems, for sending and/or receiving data. The system may preferably comprise at least one display and/or an operating keyboard as well as any other digital equipment usually connected to digital systems, e.g. printers.

In an embodiment of the system of the invention it further comprises a digital memory storing a calibration map for one or more of the isotopes $^{23}$Na isotope, $^{51}$V isotope and $^{63}$Cu isotope, the map comprises calibration data for said one or more isotopes and optionally of amounts thereof in oil.

In an embodiment the system of the invention further comprises a digital memory calibration map for one or more of the isotopes $^{23}$Na isotope, $^{51}$V isotope and $^{63}$Cu isotope, the map comprises calibration data for said one or more isotopes and optionally of amounts thereof in oil.

In an embodiment the system of the invention is configured to perform NMR measurement on an oil part in flowing condition such as it is described above.

In an embodiment the system of the invention is configured to perform NMR measurement on an oil part in form of a withdrawn sample.

In an embodiment the system of the invention is configured to perform a NMR measurement on an oil part of an oil, and performing a quantitative and/or qualitative aluminum determination.

In an embodiment the system of the invention is configured to perform a NMR measurement on an oil part of an oil, and performing a quantitative and/or qualitative catalytic fines determination.

In an embodiment the system of the invention is configured to perform a NMR measurement on an oil part of an oil in form of a fuel, during fuelling of the fuel.

In an embodiment the system of the invention is configured to perform a NMR measurement on an oil part of an oil about to be injected into an engine.

In an embodiment the system of the invention further comprises a separator for extracting catalytic fines from the oil, the system is configured to perform a NMR measurement on an oil part of an oil about to be treated in the separator, and the system is further configured to perform a NMR measurement on an oil part of an oil after treatment in the separator. The separator may e.g. be as described above.

In an embodiment the system of the invention is configured to
i. performing a quantitative and/or qualitative determination of catalytic fines in the oil;
ii. subjecting the oil to an extraction of catalytic fines in a separator operating with a number of operating parameters comprising pressure, flow velocity and temperature;
iii. performing a quantitative and/or qualitative determination of catalytic fines in the oil;
iv. comparing the determinations performed before the extraction with the determination performed after the extraction to determine the performance of the separator; and
v. adjusting one or more of the operating parameters of the separator based on the determination of the separator performance.

The adjusting of one or more of the operating parameters of the separator based on the determination of the separator performance may for example be an automated optimization e.g. set to reach a desired separation set point.

In an embodiment the system is configured to repeat steps i-v in two or more cycles, the system further comprises a feed-back loop for adjusting one or more of the operating parameters of the separator to optimize the performance of the separator based on the determinations of the separator performance for several previous cycles.

The system may for example be arranged onboard a ship or in a refinery. The measurement of the oil before and after the separator makes it possible to determine the performance (effectiveness) of the separator and optionally to adjust operating parameters and thereby increase performance of the separator, such that risk and cost associated with aluminum/catalytic fines in oils can be even further reduced.

It should be emphasized that the term "comprises/comprising" when used herein is to be interpreted as an open term, i.e. it should be taken to specify the presence of specifically stated feature(s), such as element(s), unit(s), integer(s), step(s) component(s) and combination(s) thereof, but does not preclude the presence or addition of one or more other stated features.

All features of the inventions including ranges and preferred ranges can be combined in various ways within the scope of the invention, unless there are specific reasons not to combine such features.

BRIEF DESCRIPTION OF EXAMPLES AND DRAWINGS

The invention will be explained more fully below in connection with illustrative examples and embodiment and with reference to the drawings in which:

FIG. 6 is a graph showing the relation between catalytic fines determined by a standard laboratory analysis and Al determined using NMR.

FIGS. 7a, 7b and 7c are graphical illustrations of the relation between Al and Si for use in a calibration map.

The figures are schematic and may be simplified for clarity. Throughout, the same reference numerals are used for identical or corresponding parts.

Figure 1:
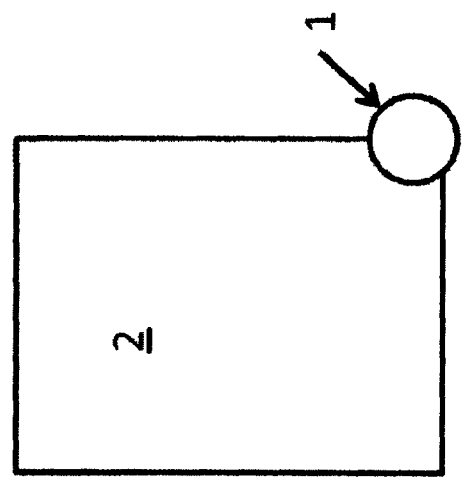
FIG. 1 is a schematic drawing of a system of the invention for determining catalytic fines in an oil tank.

FIG. 1 is a schematic illustration of a system suitable for determining catalytic fines in an oil according to the invention. The system comprises a NMR spectrometer 1, preferably as described above. The system further comprises a not shown a digital memory storing a calibration map comprising calibrating data for calibrating NMR spectra obtained by the NMR spectrometer and a computer programmed to analyze the NMR spectra obtained by the NMR spectrometer using calibration map and performing at least one quantitative and/or qualitative catalytic fines determination.

The digital memory may be integrated in the computer. The spectrometer 1 is arranged to perform NMR measurements on the oil in the oil tank 2. The spectrometer 1 is specifically arranged to perform NMR measurement on an oil part at the bottom and close to a corner of the oil tank 2.

Figure 2:
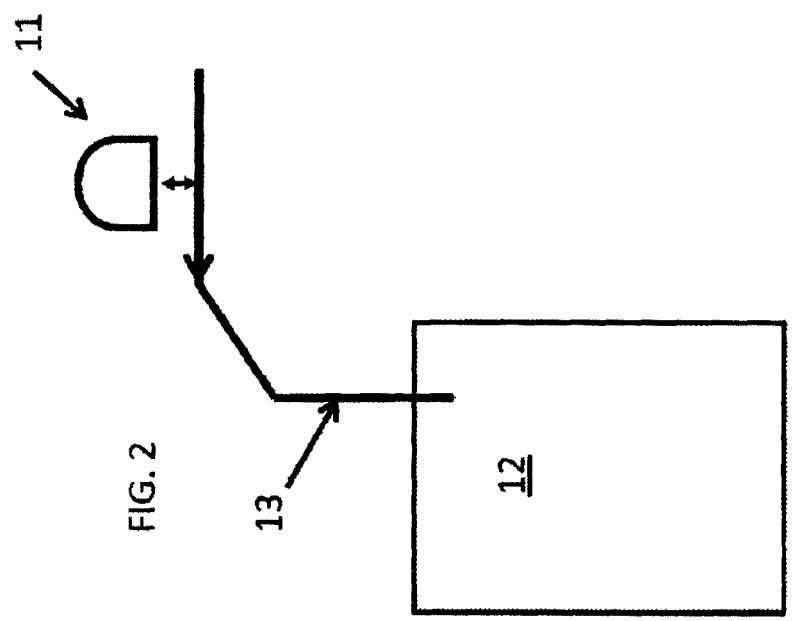
FIG. 2 is a schematic drawing of a system of the invention for determining catalytic fines in an oil under fuelling.

FIG. 2 is a schematic illustration of another system suitable for determining catalytic fines in an oil according to the invention. The system comprises a NMR spectrometer 11, preferably as described above. The system further comprises a not shown a digital memory storing a calibration map and a not shown computer.

The spectrometer 11 is arranged to perform NMR measurements on the oil in the pipe 13, which is under fuelling into oil tank 12.

In a variation thereof the pipe section 13 comprises a not shown loop branched pipe section leading a part of the oil to the NMR spectrometer 11 and back to the pipe section 13.

Figure 3:
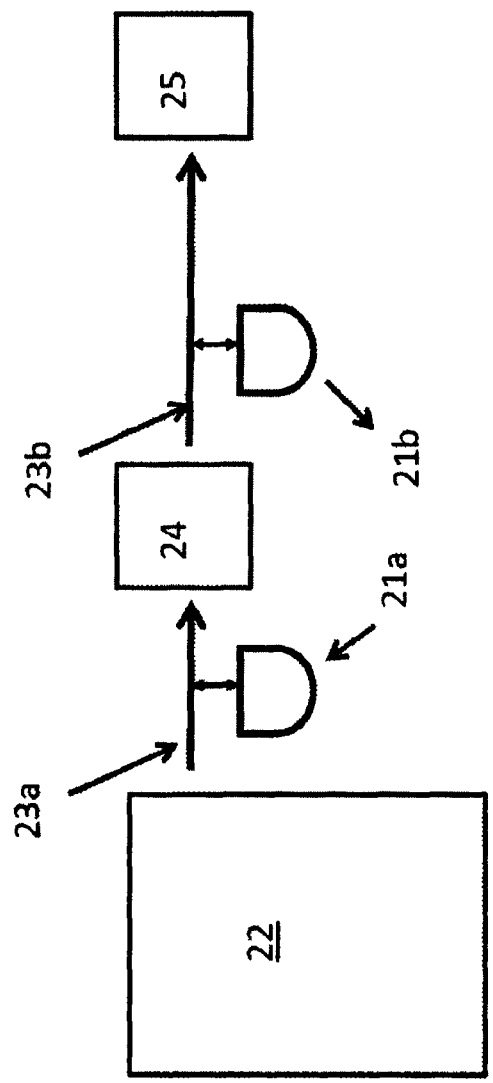
FIG. 3 is a schematic drawing of a system of the invention for determining catalytic fines in an oil transported from an oil tank to a point of use.

FIG. 3 is a schematic illustration of another system suitable for determining catalytic fines in an oil according to the invention. The system comprises a first NMR spectrometer 21a, and second spectrometer 21b. The spectrometers are connected to not shown digital memory and computer as described above.

The system further comprises a separator 24 for extracting catalytic fines, preferably as described above.

The system is configured to quantitative and/or qualitative determination of catalytic fines in the oil transported in the pipe 23a, 23b from an oil tank 22 to for example an engine via the pipe 23a and 23b. The oil is transported via pipe section 23a where the first NMR spectrometer 21a is arranged to perform determinations of catalytic fines.

The NMR spectrometer 21a may be arranged to perform determinations of catalytic fines directly on the oil flowing in the pipe section 23a. In a variation thereof the pipe section 23a comprises a not shown loop branched pipe section leading a part of the oil to the NMR spectrometer 21a and back to the pipe section 23a.

The oil is transported through the separator 24 for purification in form of extraction of catalytic fines. From the separator 24 the oil is transported via pipe section 23b where the second NMR spectrometer 21b is arranged to perform determinations of catalytic fines.

The NMR spectrometer 21b may be arranged to perform determinations of catalytic fines directly on the oil flowing in the pipe section 23ba. In a variation thereof the pipe section 23b comprises a not shown loop branched pipe section leading a part of the oil to the NMR spectrometer 21b and back to the pipe section 23b.

From the second NMR spectrometer 21b the oil is transported further e.g. to a point of use 25 e.g. an engine.

The catalytic fine determinations obtained from the first and the second NMR spectrometers 21a, 21b are compared and are used to determine the performance of the separator. The operating parameters such as pressure, flow velocity and temperature of the separator 24 can additionally be adjusted based on the determinations obtained from the first and the second NMR spectrometers 21a, 21b e.g. as described above.

Figure 4:
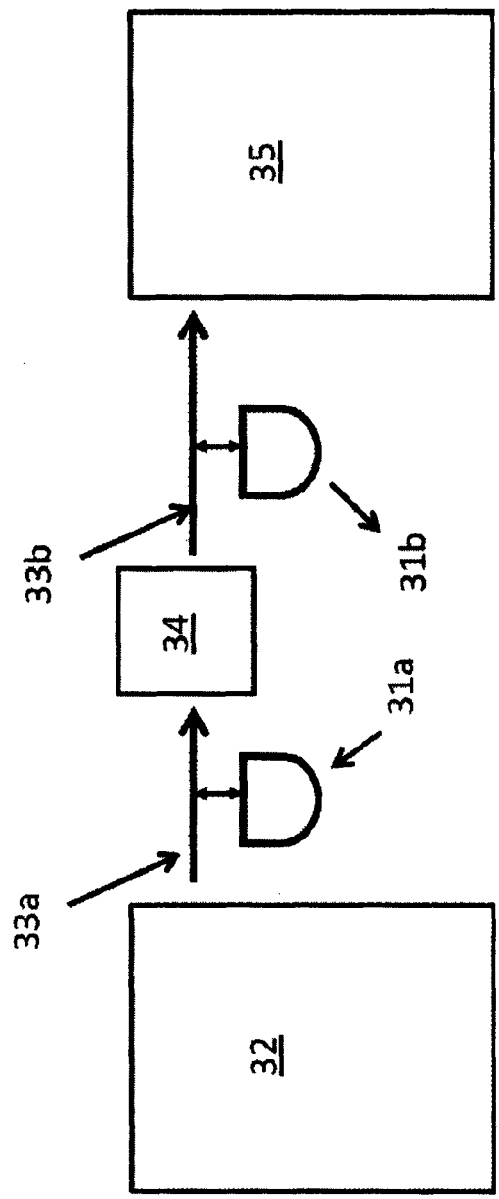
FIG. 4 is a schematic drawing of a system of the invention for determining catalytic fines in an oil transported from one tank to another.

FIG. 4 is a schematic illustration of another system suitable for determining catalytic fines in an oil according to the invention. The system comprises a first NMR spectrometer 31a, and second spectrometer 31b. The spectrometers are connected to not shown digital memory and computer as described above.

The system further comprises a separator 34 for extracting catalytic fines, preferably as described above.

The system is configured to quantitative and/or qualitative determination of catalytic fines in the oil transported in the pipe 33a and 33b from an oil tank 32, e.g. a holding tank (storage tank) to a second oil tank 32, e.g. a day tank.

A day tank is a fuel containment unit designed for installation in close-proximity to an engine to provide a reliable supply of diesel fuel onboard a vessel. Although the holding tank 32 and the day tank 35 are drawn with same size in FIG. 4, it should be understood that a day tank is usually much smaller than a holding tank.

The oil is withdrawn from the oil tank 32 and is transported via pipe section 33a where the first NMR spectrometer 31a is arranged to perform determinations of catalytic fines either directly on the pipe section 33a or on a not shown loop branched pipe section of pipe section 33a. The oil will be transported through the separator 34 for purification in the form of extraction of catalytic fines. From the separator 34 the oil is transported via pipe section 33b where the second NMR spectrometer 31b is arranged to perform determinations of catalytic fines either directly on the pipe section 33b or on a not shown loop branched pipe section of pipe section 33b. From the second NMR spectrometer 31b the oil is transported to the oil tank 35, for example a day tank.

The catalytic fine determinations obtained from the first and the second NMR spectrometers 31a, 31b are compared and are used to determine the performance of the separator. The operating parameters such as pressure, flow velocity and temperature of the separator 34 can additionally be adjusted based on the determinations obtained from the first and the second NMR spectrometers 31a, 31b e.g. as described above.

Figure 5:
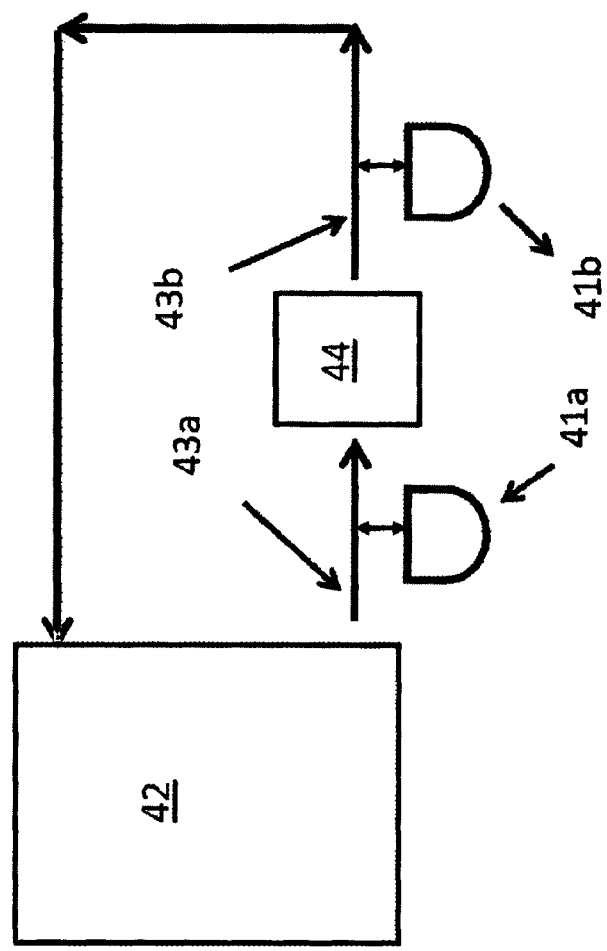
FIG. 5 is a schematic drawing of a system of the invention for determining catalytic fines in an oil withdrawn from an oil tank.

FIG. 5 is a schematic illustration of another system suitable for determining catalytic fines in an oil according to the invention. The system comprises a first NMR spectrometer 41a, and second spectrometer 41b. The spectrometers are connected to not shown digital memory and computer as described above.

The system further comprises a separator 44 for extracting catalytic fines, preferably as described above.

The system is configured to quantitative and/or qualitative determination of catalytic fines in the oil transported in the pipe 43a and 43b from an oil tank 42 to the same oil tank 42.

The oil is withdrawn from the oil tank 42 and is transported via pipe section 43a where the first NMR spectrometer 41a is arranged to perform determinations of catalytic fines either directly on the pipe section 43a or on a not shown loop branched pipe section of pipe section 43a. The oil will be transported through the separator 44 for purification in the form of extraction of catalytic fines. From the separator 44 the oil is transported via pipe section 43b where the second NMR spectrometer 41b is arranged to perform determinations of catalytic fines either directly on the pipe section 43b or on a not shown loop branched pipe section of pipe section 43b. From the second NMR spectrometer 41b the oil is transported back to the oil tank 42, for example in a top part of the oil tank 42.

EXAMPLE 1

Calibration Map

A statistically significant number of different heavy fuel oil samples with varying amounts of catalytic fines, i.e. alumina/silica particles, are subjected to standard laboratory analysis of aluminum and silicon according to ISO standard 10478.

The spread of the concentration of aluminum/silicon in theses samples should cover the naturally found range, i.e. the range from 5-150 mg/kg aluminum and 10-250 mg/kg silicon corresponding to the limits given in ISO 10478.

Aliquots of these samples are analyzed in parallel given the NMR based method described.

A correlation analysis of both datasets (laboratory vs. NMR) will show a correlation of the type $y=a*x+b$. The coefficients of this linear equation are used as a calibration map for calculating the true aluminum content of a given sample from its NMR signal.

An example of expected results is shown in FIG. 6.

The line indicates what should have been expected. However, in the shown example in FIG. 6, the NMR method provides a higher signal of aluminum that the actual amount determined according to ISO standard 10478. The NMR measurements can accordingly be calibrated.

EXAMPLE 2

Calibration Map

Total amount of catalytic fines (Si+Al) determined in form of ppm was determined on a large amount of HFO samples (185308), here in the form of bunkering. The determinations were performed using standard methods according to ISO standard 10478.

Figure 7A:
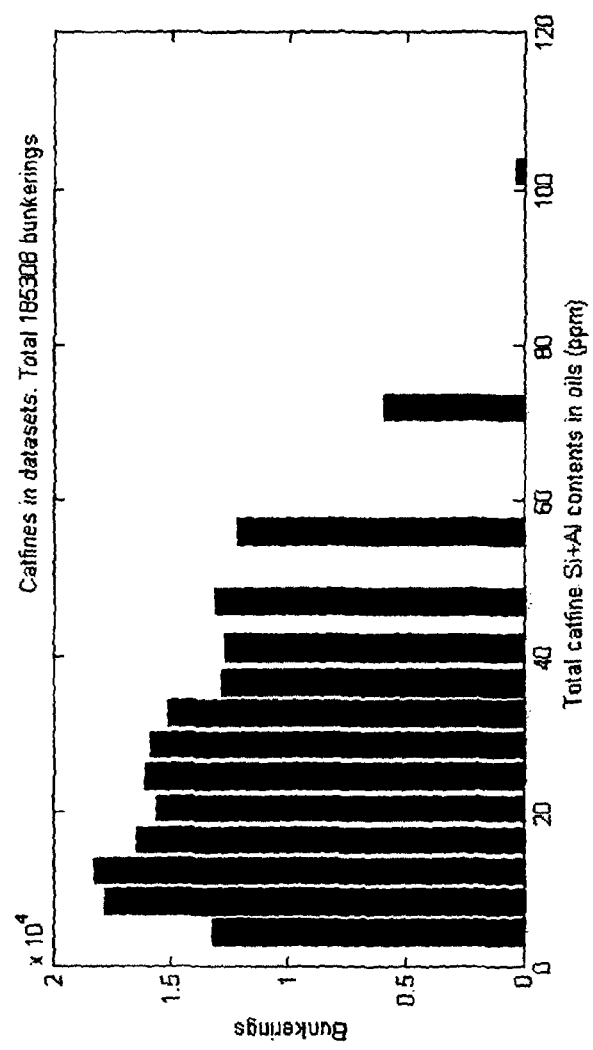

The results shown in FIG. 7a show that the amount of catalytic fines in the bunkerings tested varies between about 5 and 75 ppm.

The respective amount of Al and Si was determined in the bunkering sample where the catalytic fines were >30 ppm. The number of bunkering included in this test was 76156.

Figure 7B:
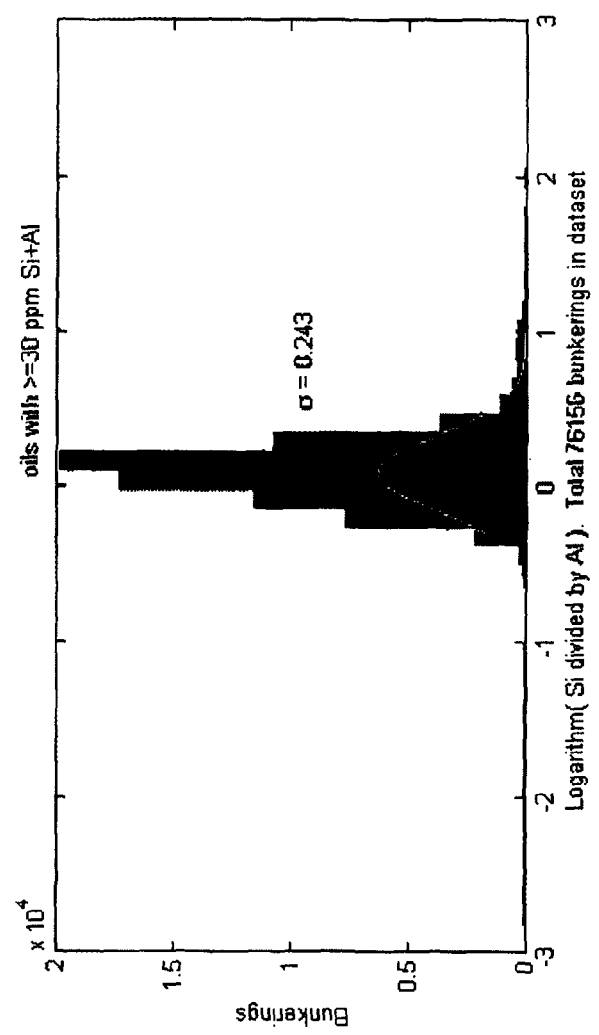

The relation between catalytic fines and aluminum was plotted as log (amount Si/amount Al) as shown in FIG. 7b.

As it can be seen the obtained curve is a Gaussian distribution around 0.

In FIG. 7c the curve 41 shows the mean value of Si/al ratio. The curve 42 is a model of Lab assuming+2 ppm/95% for each parameter and curves 43 and 44 show the 95% confidence curve, indicating that the ratio between Al and Si in 95% of the determinations is in the interval between the curves 43 and 44.

EXAMPLE 3

NMR Measurement

A number of measurements were determined according to the method as shown below.

| | |
|---|---|
| Magnetic field strength | About 1.6 T |
| Oil sample | Bunker fuel flowing in a pipe with an inner diameter of 12 mm and a velocity of about 1 l/min. |
| Measuring volume (oil part) | 0.005 L |
| Exciting RF pulse | 90 degree pulse. Band width of about 200 KHz with centre about 16.5 MHz. |
| Refocusing pulses | Trains of 180 degree pulses. Band width of about 200 KHz with centre about 16.5 MHz. |
| TW | About 15 ms |
| TE | About 75 µs |
| Antenna Q (quality-factor) | About 50 |
| Exciting RF power | About 100 W |
| Measurement time | About 1 Hour |

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Some preferred embodiments have been shown in the foregoing, but it should be stressed that the invention is not limited to these, but may be embodied in other ways within the subject-matter defined in the following claims.

What is claimed is:

1. A method of performing a quantitative and/or qualitative determination of catalytic fines in fuel oil, the method comprises determining aluminum using NMR and quantitative and/or qualitative determination of the catalytic fines based on the aluminum determination, the method comprises determining aluminum in the form of aluminum isotope $^{27}$Al by performing at least one NMR measurement on a part of the oil, obtaining at least one NMR spectrum from the NMR measurement(s) and determining the catalytic fines quantitatively and/or qualitatively using said aluminum determination.

2. The method of claim 1, wherein the NMR measurement is performed on the oil part in flowing condition.

3. The method of claim 1, wherein the NMR measurement is performed in-line or semi-in-line, comprising performing the NMR measurement onboard a motor driven unit.

4. The method of claim 1, wherein the NMR measurement comprises withdrawing the oil part as a sample of the oil and performing the NMR measurement on the withdrawn sample.

5. The method of claim 1, wherein the method comprises determining catalytic fines in the oil, subjecting the oil to a catalytic fine extraction treatment, and repeating the determination of catalytic fines in the oil.

6. The method of claim 1, wherein the NMR measurement comprises simultaneously subjecting the oil part to a magnetic field B, and a plurality of pulses of radio frequency energy E (RF pulses) and receiving electromagnetic signals from the aluminum isotopes.

7. The method of claim 6, wherein the magnetic field B is between about 1 Tesla and about 3 Tesla.

8. The method of claim 6, wherein the method comprises performing a plurality of NMR measurements at a selected magnetic field, the magnetic field is kept substantially stationary during the plurality of NMR measurements.

9. The method of claim 1, wherein the method comprises performing a plurality of NMR measurement on the same oil.

10. The method of claim 1, wherein the NMR measurement comprises simultaneously subjecting the oil part to a magnetic field B, and an exciting RF pulse with frequencies selected to excite a nuclei spin of at least a part of the aluminum isotopes.

11. The method of claim 10, wherein the frequency range of the exciting RF pulse spans over at least about 10000 ppm.

12. The method of claim 10, wherein the frequency range of the exciting RF pulse comprises a band width of at least about 1 MHZ.

13. The method of claim 1, wherein the method comprises determining at least one relaxation rate of an exited aluminum isotope.

14. The method of claim 13, wherein the method comprises determining at least one spin-lattice—T1 relaxation value of an exited aluminum isotope.

15. The method of claim 13, wherein the method comprises determining at least one spin-spin—T2 relaxation value of an exited aluminum isotope.

16. The method of claim 1, wherein the method comprises subjecting the oil part to pulsed trains of RF pulses, with repetition rates of at about 100 ms or less.

17. The method of claim 1, wherein the NMR measurement comprises simultaneously subjecting the oil part to a magnetic field B, and a plurality of RF pulses wherein the RF pulses comprise
   i. an exciting RF pulse, and
   ii. at least one refocusing RF pulse.

18. The method of claim 17 wherein the exciting RF pulse is in form of a 90° pulse and the refocusing RF pulse(s) is in the form of a 180° pulse.

19. The method of claim 18, wherein the refocusing RF pulse(s) is/are applied with an echo-delay time after the exciting RF pulse, the echo-delay time is of about 50 μs or less.

20. The method of claim 18, wherein the at least one refocusing pulse comprises a plurality of refocusing pulses or trains of refocusing pulses applied with refocusing delay (TE) intervals between two consecutive refocusing pulses.

21. The method of claim 1, wherein the method comprises obtaining at least one NMR spectrum comprising an NMR spectrum from −500 ppm or less to +500 ppm in relation to a reference Al-composition, wherein the reference Al-composition preferably is Zeolite Y.

22. The method of claim 1, wherein the method comprises determining quantitatively and/or qualitatively at least one compound comprising an aluminum isotope.

23. The method of claim 1, wherein the determination of catalytic fines comprises a quantitative and/or qualitative determination of at least one aluminum containing compound and/or at least one aluminum containing complex.

24. The method of claim 1 comprising maintaining the temperature at a selected value.

25. The method of claim 1, wherein the quantitative and/or qualitative aluminum determination is performed by providing a calibration map of known aluminum containing compound(s) and of amounts thereof in oil.

26. The method of claim 1, wherein the method comprises preparing calibration data, the calibration data is stored on a digital memory, the method comprises feeding the NMR spectrum(s) or data obtained from the NMR spectrum(s) to a computer in digital communication with the digital memory and providing the computer to compare and analyze the data to perform at least one quantitative and/or qualitative aluminum determination.

27. The method of claim 1, wherein the method further comprises performing a sodium determination of measurement on the oil part using NMR by determining $^{23}$Na isotope by performing at least one NMR measurement on the oil part, obtaining at least one NMR spectrum from the NMR measurement(s) and performing at least one quantitative and/or qualitative sodium determination.

28. The method of claim 1, wherein the method further comprises performing a vanadium determination of measurement on the oil part using NMR by determining $^{51}$V isotope by performing at least one an NMR measurement the oil part, obtaining at least one NMR spectrum from the NMR measurement(s) and performing at least one quantitative and/or qualitative vanadium determination.

29. The method of claim 1, wherein the fuel oil is a heavy fuel oil (HFO).

30. The method of claim 1, wherein the method comprises
   i. performing a quantitative and/or qualitative determination of catalytic fines in the oil;
   ii. extracting catalytic fines from the oil; and
   iii. performing a quantitative and/or qualitative determination of catalytic fines in the oil.

31. The method of claim 30 wherein the method comprises
   i. performing a quantitative and/or qualitative determination of catalytic fines in the oil;
   ii. subjecting the oil to an extracting of catalytic fines in a separator operating with a number of operating parameters comprising pressure, flow velocity and temperature;
   iii. performing a quantitative and/or qualitative determination of catalytic fines in the oil;
   iv. comparing the determinations performed before the extraction with the determination performed after the extraction to determine the performance of the separator; and
   v. adjusting one or more of the operating parameters of the separator based on the determination of the separator performance.

32. A method of performing a quantitative and/or qualitative determination of catalytic fines in fuel oil, the method comprising
   i. performing a quantitative and/or qualitative determination of catalytic fines in the oil;
   ii. subjecting the oil to an extracting of catalytic fines in a separator operating with a number of operating parameters comprising pressure, flow velocity and temperature;
   iii. performing a quantitative and/or qualitative determination of catalytic fines in the oil;
   iv. comparing the determinations performed before the extraction with the determination performed after the extraction to determine the performance of the separator; and
   v. adjusting one or more of the operating parameters of the separator based on the determination of the separator performance;
   wherein steps i-v are repeated in two or more cycles and the determinations of the separator performance for several previous cycles are used in the step of adjusting one or more of the operating parameters of the separator to optimize the performance of the separator and
   wherein the quantitative and/or qualitative determination of catalytic fines comprises determining aluminum using NMR and quantitative and/or qualitative determination of the catalytic fines based on the aluminum determination.

33. A system suitable for determining catalytic fines in a fuel oil comprising determining aluminum using isotope $^{27}$Al NMR and quantitative and/or qualitative determination of the catalytic fines based on the aluminum determination, the system comprises a NMR spectrometer, a digital memory storing a calibration map comprising calibrating data for calibrating NMR spectra obtained by the NMR spectrometer and a computer programmed to analyze the NMR spectra obtained by the NMR spectrometer using calibration map and performing at least one quantitative and/or qualitative catalytic fines determination, wherein the system further comprises a separator for extracting catalytic fines from the oil, the system is configured to perform a NMR measurement on an oil part of an oil about to be treated in the separator, and the system is further configured to perform a NMR measurement on an oil part of an oil after treatment in the separator.

34. The system of claim 33 further comprising a digital memory storing a calibration map for one or more of the isotopes $^{23}$Na isotope, $^{51}$V isotope and $^{63}$Cu isotope, the map comprises calibration data for said one or more isotopes.

35. The system of claim 33, wherein the system is configured to perform NMR measurement on an oil part in flowing condition.

36. The system of claim 33, wherein the system is configured to perform NMR measurement on an oil part in form of a withdrawn sample.

37. The system of claim 33, wherein the system is configured to perform a NMR measurement on an oil part of an oil, and perform a quantitative and/or qualitative aluminum determination.

38. The system of claim 33, wherein the system is configured to perform a NMR measurement on an oil part of an oil in form of a fuel, during fuelling of the fuel.

39. The system of claim 33, wherein the system is configured to
  i. performing a quantitative and/or qualitative determination of catalytic fines in the oil;
  ii. subjecting the oil to an extracting of catalytic fines in a separator operating with a number of operating parameters comprising pressure, flow velocity and temperature;
  iii. performing a quantitative and/or qualitative determination of catalytic fines in the oil;
  iv. comparing the determinations performed before the extraction with the determination performed after the extraction to determine the performance of the separator; and
  v. adjusting one or more of the operating parameters of the separator based on the determination of the separator performance.

40. The system of claim 33, wherein the system is configured to repeat steps i-v in two or more cycles, the system further comprises a feed-back loop for adjusting one or more of the operating parameters of the separator to optimize the performance of the separator based on the determinations of the separator performance is for several previous cycles.

41. A method of performing a quantitative determination of catalytic fines in fuel oil, the method comprising performing at least one aluminum isotope $^{27}$Al NMR measurement on a part of the oil, obtaining at least one NMR spectrum from the NMR measurement(s) and determining from the NMR spectrum if the amount of catalytic fines is less than a recommended level of 60 ppm W/W or less.

42. The method of claim 41, wherein the method comprises determining if the amount of catalytic fines is less than a recommended level of 15 ppm W/W.

43. The method of claim 41, wherein the method comprises determining the amount of aluminum in the oil and correlating the mount of aluminum to obtain the amount of catalytic fines.

44. The method of claim 41, wherein the method comprises
  i. determining if the amount of catalytic fines in the oil is less than a recommended level of 60 ppm or less and if not
  ii. extracting catalytic fines from the oil,
and repeating the steps i and ii until the amount of catalytic fines in the oil is less than the recommended level.

* * * * *